United States Patent [19]

Baur et al.

[11] Patent Number: 5,206,443

[45] Date of Patent: Apr. 27, 1993

[54] ALKANEDIOL BISACETALS

[75] Inventors: Richard Baur, Mutterstadt; Helmut Guembel, Ludwigshafen; Alfred Oftring, Bad Durkheim; Johannes Perner, Neustadt; Gerhard Wolf, Mannheim, all of Fed. Rep. of Germany

[73] Assignee: BASF Aktiengesellschaft, Ludwigshafen, Fed. Rep. of Germany

[21] Appl. No.: 871,093

[22] Filed: Apr. 20, 1992

[30] Foreign Application Priority Data

Apr. 23, 1991 [DE] Fed. Rep. of Germany ........ 4113163

[51] Int. Cl.$^5$ .................. C07C 43/11; C07C 43/15
[52] U.S. Cl. .................... 568/598; 568/600; 568/601
[58] Field of Search ............. 568/596, 598, 601, 600

[56] References Cited

U.S. PATENT DOCUMENTS 2,905,719  9/1959  de Benneville et al. ............ 568/601
3,931,337  1/1976  Langdon ............................ 568/601

FOREIGN PATENT DOCUMENTS 0570841   2/1959  Canada ................................ 568/601
2252186   5/1974  Fed. Rep. of Germany .
3318592  11/1984  Fed. Rep. of Germany ...... 568/601
2204683   5/1974  France .

Primary Examiner—Marianne M. Cintins
Assistant Examiner—Margaret J. Page
Attorney, Agent, or Firm—Oblon, Spivak, McClelland, Maier & Neustadt

[57] ABSTRACT

Alkanediol bisacetals useful as surface-active substances for industrial purposes, in particular in washing and cleaning agents, have the formula I

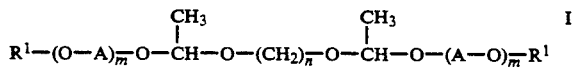

where
  $R^1$ is alkyl or alkenyl of from 6 to 30 carbon atoms,
  A is 1,2-alkylene of from 2 to 4 carbon atoms,
  m is from 0 to 50,
  within each of the pairs $R^1$, A and m the meanings being identical or different, and
  n is from 2 to 20.

5 Claims, No Drawings

ALKANEDIOL BISACETALS

The present invention relates to novel alkanediol bisacetals of the general formula I

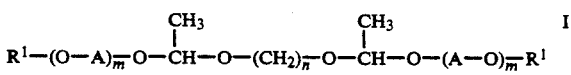

where
R$^1$ is alkyl or alkenyl of from 6 to 30 carbon atoms,
A is 1,2-alkylene of from 2 to 4 carbon atoms,
m is from 0 to 50,
within each of the pairs R$^1$, A and m the meanings being identical or different, and
n is from 2 to 20.

The present invention also relates to a process for preparing the alkanediol bisacetals, to the use thereof as surface-active substances for industrial purposes, in particular in washing and cleaning agents, and also to washing and cleaning agents containing compounds I.

Washing and cleaning processes in industry, commercial enterprises and the home are today more than ever in need of surface-active substances possessing in particular good alkali stability, low-foam properties and an effective antifoam effect, in particular in the case of mechanized cleaning processes.

DE-A-2 252 186 proposes compounds of the type

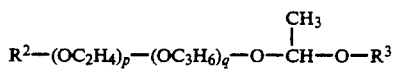

where R$^2$ is a long-chain alkyl radical or an alkylaryl radical, R$^3$ is a shorter alkyl radical, and p and q are from 1 to 30 and from 5 to 50 respectively. However, such alkoxylates with a monoacetal structure prove to be still in need of improvement in their washing and cleaning properties.

It is an object of the present invention to remedy the above-described defects of the prior art.

We have found that this object is achieved by the alkanediol bisacetals I defined in the opening paragraph.

As straight-chain or branched alkyl and alkenyl groups R$^1$ there may be mentioned for example: n-hexyl, n-heptyl, n-octyl, 2-ethylhexyl, n-nonyl, isononyl, n-decyl, isodecyl, n-undecyl, n-dodecyl, n-tridecyl, isotridecyl, n-tetradecyl, n-pentadecyl, n-hexadecyl, n-heptadecyl, n-octadecyl, n-eicosyl, oleyl, linolyl and linolenyl. R$^1$ is preferably straight-chain or only slightly branched; that is, it contains not more than 3 methyl or ethyl side chains.

Depending on the origin of the alcohol used in the synthesis of the compounds I, R$^1$ is a radical of a naturally occurring fatty alcohol or preferably of a synthetically produced oxo or Ziegler alcohol. Examples of readily usable alcohols produced by the oxo process are $C_{10}$-, $C_{13}$- and $C_{15}$-alcohols and also $C_9/C_{11}$-, $C_{10}/C_{12}$-, $C_{12}/C_{14}$-, $C_{13}/C_{15}$- and $C_{16}/C_{18}$-alkanol mixtures. Examples of readily usable alcohols produced by the Ziegler process are $C_8/C_{10}$-, $C_{10}/C_{12}$-, $C_{12}/C_{14}$-, $C_{16}/C_{18}$- and $C_{12}/C_{16}$-, $C_{16}/C_{20}$-alkanol mixtures.

Since the alcohols used in the synthesis of the compounds I are in general random homolog mixtures and also isomer mixtures, it is advisable to speak of an average number of carbon atoms in connection with the R$^1$ radicals.

Preference is given to compounds I where R$^1$ is alkyl or alkenyl of from 9 to 18 carbon atoms, in particular of from 10 to 16 carbon atoms. Of particular advantage are those radicals R: which can be traced back to the $C_{10}$-fraction, the $C_{13}$-fraction or the $C_{10}/C_{12}$-, the $C_{12}/C_{14}$-, the $C_{13}/C_{15}$- or the $C_{16}/C_{18}$-cut of an alcohol obtained by the oxo process.

The 1,2-alkylene group A is in particular ethylene but may also be propylene, 1,2-butylene or 2,3-butylene. Each group A may in fact constitute a random mixture of more than one of the 1,2-alkylene groups mentioned or a group composed of up to three uniform blocks of these alkylene groups; however, preference is given to 1,2-alkylene groups A which contain only a single unit.

The degrees of alkoxylation m are within the range from 0 to 50, preferably from 2 to 15, in particular from 3 to 12. The values for m are customarily averages.

The variables R$^1$, A and m are in each case preferably identical, so that the compounds I are symmetrical molecules.

The number of methylene bridge members n is from 2 to 20, preferably from 2 to 10, in particular from 2 to 6; very particular preference is given to the number 4.

Advantageously, the alkanediol bisacetals I are prepared by reacting alkanediol bisvinyl ethers of the general formula II

where n is as defined above, with alkoxylated alcohols of the general formula III

where R$^1$, A and m are each as defined above, or with a mixture of such alcohols at from 0° to 100° C. in the presence of a catalytic amount of an acid.

The reaction is preferably carried out at from 10° to 60° C., in particular from 20° to 40° C., and in general at atmospheric pressure. An additional inert solvent or diluent is normally not necessary, but may be added if necessary, for example in the case of viscosity problems. An essential prerequisite for a clean reaction without by-products is the substantial absence of water and lower alcohols.

The reaction of the bisvinyl ethers II with the alkoxylates III is carried out under acid catalysis. Suitable catalysts include not only Lewis acids, eg. $BF_3$, $AlCl_3$, $ZnCl_2$ or $TiCl_4$, but also mineral acids, e.g. HCl, $H_2SO_4$, $H_3PO_4$, $H_3PO_3$ or $HClO_4$. It is similarly possible to use organic carboxylic and sulfonic acids, e.g. methane-sulfonic acid, p-toluenesulfonic acid, oxalic acid, formic acid, acetic acid, propionic acid or dodecylbenzene-sulfonic acid. It is of particular advantage to use p-toluenesulfonic acid as catalyst.

The acidic catalyst is used in the reaction in customary amounts, i.e. normally in an amount of about 0.1–5 mol%, based on alkoxylate III used. After the reaction, the acidic catalyst can be neutralized with inorganic bases, e.g. NaOH, KOH, $K_2CO_3$, or $Na_2CO_3$, or organic bases, e.g. trimethylamine, triethylamine, dimethylcyclohexylamine, pyridine or the reaction product of ethylenediamine with 4 mol of propylene oxide.

The course of the reaction is conveniently monitored by means of IR spectroscopy, the decrease in or the complete disappearance of the O—H stretching vibration of the alkoxylated alcohols III used serving as criterion for completion of the reaction.

The alkoxylated alcohols III can be prepared in a conventional manner by alkoxylating the corresponding abovementioned fatty alcohols, oxo alcohols or Ziegler alcohols.

The alkanediol bisvinyl ethers II can likewise be prepared in a conventional manner from the corresponding diols by addition to acetylene.

The alkanediol bisacetals I according to the present invention are in general suitable for use as surface-active substances for industrial purposes and thus have a multiplicity of technical applications. Possible areas of use are for example the washing and cleaning detergent industry, the electroplating industry, the photographic industry, the textile industry, the paper industry, oil production, the pharmaceutical industry, the cosmetic industry, the food industry and plant nutrition.

The compounds I according to the present invention are especially suitable for use as surface-active substances in washing and cleaning agents for industry, the catering trade and the home, in particular for mechanized cleaning processes in the metal, paper, textile or food industry, for example for industrial bottle washing or for mechanized dish washing.

Bottles are cleaned in the beverage industry using highly alkaline cleaners. The alkali dissolves, neutralizes and/or saponifies drink residues, and converts the label glue into a strongly foaming water-soluble form. All these processes are accompanied by a great deal of mechanical agitation and thus augment the already considerable foaming tendency of starch and sugar degradation products.

Another use concerns industrial cleaning processes in the metal industry. Here too a thoroughly wetting alkaline aqueous solution is employed under high pressure as a cleaning medium for removing drawing and rolling greases or carboxyl-containing organic corrosion inhibitors. Here the surfactants according to the present invention will not only improve the wetting properties but in particular contribute to suppressing the foam due for example to anionic surfactants of the type of the alkylbenzenesulfonates or of other sulfo- and carboxyl-containing surfactants.

The present invention also provides washing and cleaning agents which, as well as the constituents customary for this purpose, contain from 0.1 to 50% by weight, preferably from 1 to 30% by weight, based on the total amount of the formulation, of one or more alkanediol bisacetals I according to the present invention. The constituents and compositions of such washing and cleaning agents are known to the person skilled in the art and therefore need not be more particularly described herein.

The alkanediol bisacetals I according to the present invention are alkali-stable and notable for their excellent application properties such a efficient lowering of surface tension, good wetting power, absence of foam and in particular efficient foam suppression coupled with good biodegradability of in general at least 80%.

Preparation examples

EXAMPLE 1

408.9 g (corresponding to 1.0 mol) of the product of reacting 5 mol of ethylene oxide with a $C_{13}$-oxo alcohol (OH number: 137.2 mg of KOH/g) were dehydrated with 3.8 g (corresponding to 0.02 mol) of p-toluenesulfonic acid monohydrate at 100° C. and about 10 mbar in the course of 2 hours. The mixture was cooled down to 20°–25° C. and admixed at that temperature with 77.1 g (corresponding to 0.5 mol) of 1,4-butanediol bisvinyl ether, added dropwise over 2 hours. The mixture was subsequently stirred at room temperature for 20 minutes and the catalyst was neutralized with 2.5 g (corresponding to 0.02 mol) of dimethylcyclohexylamine. Filtration gave 472 g of product (corresponding to a yield of 97%) having an OH number of 2.9 mg of KOH/g.

EXAMPLES 2 TO 14

The method of Example 1 was also used to react the alkoxylated alcohols listed in Table 1 with 1,4-butanediol bisvinyl ether to give the products 2 to 14.

TABLE 1

Alkanediol bisacetals formed from alkoxylated alcohols and 1,4-butanediol bisvinyl ether

| Example No. | Alcohol | Degree of ethoxylation m | Product OH number [mg of KOH/g] | Yield [%] |
| --- | --- | --- | --- | --- |
| 2 | $C_{13}$-oxo alcohol | 3 | 3.1 | 95 |
| 3 | $C_{13}$-oxo alcohol | 12 | 2.9 | 93 |
| 4 | $C_{13}/C_{15}$-oxo alcohol | 3 | 5.8 | 97 |
| 5 | $C_{13}/C_{15}$-oxo alcohol | 5 | 6.9 | 95 |
| 6 | $C_{13}/C_{15}$-oxo alcohol | 7 | 3.3 | 94 |
| 7 | $C_{13}/C_{15}$-oxo alcohol | 10 | 3.3 | 95 |
| 8 | $C_{10}$-oxo alcohol | 3 | 6.3 | 97 |
| 9 | $C_{10}$-oxo alcohol | 5 | 4.8 | 93 |
| 10 | $C_{10}$-oxo alcohol | 7 | 3.6 | 94 |
| 11 | $C_{10}$-oxo alcohol | 11 | 3.5 | 95 |
| 12 | $C_{10}/C_{12}$-oxo alcohol | 6 | 8.0 | 96 |
| 13 | $C_{12}/C_{14}$-oxo alcohol | 3 | 5.0 | 96 |
| 14 | $C_{16}/C_{18}$-oxo alcohol | 9 | 5.0 | 97 |

Application properties

The foaming power was tested in accordance with DIN 53 902 at 40° C. using 2 g of in-test substance/l by determining the volume of foam in ml 30 sec after termination of the foam generation.

By way of further characterization, the wetting power was examined in accordance with DIN 53 901 by dipping a cotton fabric into the surfactant solution to be examined. The measurement was carried out with 2 g of in-test substance/l and 2 g of sodium carbonate/l in distilled water at 20° C. by measuring the time in sec until the fabric loses its buoyancy due to the entrapped air and begins to sink. The shorter the time, the better the wetting power.

The surface tension was measured in accordance with DIN 53 914 at 20° C. using 0.1 g of in-test substance/l by measuring the force in mN/m required to pull a horizontally suspended ring or stirrup from the surface of the liquid.

The foam suppression behavior was tested in line with the various requirements on the one hand in a dishwasher in the presence of egg white ("egg test") and on the other in terms of the foam-suppressing effect on the $C_{12}/C_{14}$-α-olefinsulfonate in a dynamic foaming apparatus.

In the so-called "egg test", magnetic induction measurement was used to count the number of revolutions of a spraying arm in a dishwashing apparatus (Miele model G 7735) with the aid of a counter. Foaming, which occurs in particular in the presence of proteins (egg white), reduces the speed of the arm. Thus, the number of revolutions per minute, because of the reduced thrust, represents a measure of the suitability of surfactants for use in high-agitation cleaning equipment.

The test time was 12 minutes, over which the number of revolutions per minute was calculated from the total number of revolutions. The wash was started at room temperature, but after about 10 minutes the temperature of the washing water was 60° C.

The foam-suppressing effect on $C_{12}/C_{14}$-α-olefin-sulfonate in a dynamic foaming apparatus is a laboratory method used to investigate the foam suppressing effect on anionic surfactants. The apparatus in question is a flows recirculation machine. The buildup of foam is created as a result of the fact that, within a temperature controlled, calibrated tube 10 cm in diameter, a jet flows continuously under constant pressure into the in-test solution while at the same time finely divided air is passed into the solution. If a foam booster in the form of $C_{12}/C_{14}$-α-olefinsulfonate is added to the in-test solution, foam builds up with time as a function of product, the height achieved being measured in cm after 10 minutes. The foam height relates to a use of 1000 pp, of foam booster on addition of 40 ppm of the in-test substance. The lower the foam, the higher the suppression potential of the surfactant.

Table 2 shows the results of the application tests described.

TABLE 2

Foaming power, wetting power, surface tension and foam suppression behavior of alkanediol bisacetals

| Example No. | Foaming power [ml] | Wetting power [sec] | Surface tension [mN/m] | "Egg test" [rpm] | Suppression of foam on $C_{12}/C_{14}$-α-olefinsulfonate [cm] |
|---|---|---|---|---|---|
| 1 | 10 | >300 | 28.7 | 102 | 50 |
| 2 | 0 | 67 | 28.6 | 110 | 19 |
| 3 | 80 | 63 | 30.4 | 92 | 72 |
| 4 | 10 | 95 | 29.0 | 109 | 26 |
| 5 | 10 | 65 | 29.0 | 104 | 45 |
| 6 | 40 | >300 | 29.3 | 106 | 63 |
| 7 | 50 | 160 | 30.5 | 116 | 72 |
| 8 | 0 | 100 | 29.1 | 107 | 32 |
| 9 | 0 | 68 | 29.5 | 112 | 49 |
| 10 | 10 | 85 | 29.4 | 116 | 61 |
| 11 | 50 | 85 | 31.6 | 112 | 60 |
| 12 | 20 | 95 | 29.4 | 104 | 59 |
| 13 | 0 | >300 | 29.2 | 105 | 47 |

TABLE 2-continued

Foaming power, wetting power, surface tension and foam suppression behavior of alkanediol bisacetals

| Example No. | Foaming power [ml] | Wetting power [sec] | Surface tension [mN/m] | "Egg test" [rpm] | Suppression of foam on $C_{12}/C_{14}$-α-olefinsulfonate [cm] |
|---|---|---|---|---|---|
| 14 | 0 | >300 | 32.2 | 107 | 64 |

The results of Table 2 show that, according to the foam tests of DIN 53 902, all the products invesigated, with a few exceptions, form virtually no foam.

The realistic "egg test" in the dishwasher shows that the foam-suppressing properties on foam due to the presence of protein are outstanding, since values above 80 rpm already indicate excellent foam suppression.

The wetting power values show that, depending on the degree of ethoxylation, even highly efficient foam-suppressing products give excellent wetting effects.

The products of Examples 2, 4 and 8 give foam suppression values in the dynamic foaming apparatus hitherto obtainable only with nonbiodegradable surfactants.

The alkanediol bisacetals I according to the present invention thus are products which, depending on the structure and the degree of ethoxylation, combine excellent foam suppression with good wetting effects and the absence of foam, as well as alkali stability and biodegradability.

We claim:

1. An alkanediol bisacetal of the general formula I

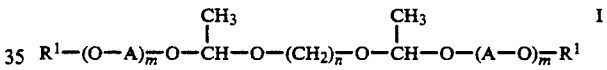

where
  $R^1$ is alkyl or alkenyl of from 6 to 30 carbon atoms,
  A is 1,2-alkylene of from 2 to 4 carbon atoms,
  m is from 0 to 50,
    within each of the pairs $R^1$, A and m the meanings being identical or different, and
  n is from 2 to 20.

2. An alkanediol bisacetal I as claimed in claim 1, wherein $R^1$ is alkyl or alkenyl of from 9 to 18 carbon atoms.

3. An alkanediol bisacetal I as claimed in claim 1, wherein A is ethylene.

4. An alkanediol bisacetal I as claimed in claim 1, wherein m is from 2 to 15.

5. An alkanediol bisacetal I as claimed in claim 1, wherein n is from 2 to 10.

* * * * *